United States Patent
Zamora

(10) Patent No.: US 7,297,343 B2
(45) Date of Patent: *Nov. 20, 2007

(54) BIOACTIVE MEDICAL FILMS

(75) Inventor: Paul O. Zamora, Gaithersburg, MD (US)

(73) Assignee: BioSurface Engineering Technologies, Inc., Rockville, MD (US)

( * ) Notice: Subject to any disclaimer, the term of this patent is extended or adjusted under 35 U.S.C. 154(b) by 469 days.

This patent is subject to a terminal disclaimer.

(21) Appl. No.: 10/684,022

(22) Filed: Oct. 10, 2003

(65) Prior Publication Data

US 2004/0151764 A1    Aug. 5, 2004

Related U.S. Application Data

(63) Continuation-in-part of application No. 10/450,309, filed on Jan. 28, 2003, now Pat. No. 6,921,811.

(60) Provisional application No. 60/418,127, filed on Oct. 10, 2002.

(51) Int. Cl.
   *A61L 15/28*   (2006.01)
   *A61K 31/727*  (2006.01)

(52) U.S. Cl. .................. 424/447; 424/445; 514/8; 514/56

(58) Field of Classification Search ............... 424/425, 424/445, 447; 514/2, 8, 56
See application file for complete search history.

(56) References Cited

U.S. PATENT DOCUMENTS

| 5,147,339 | A |   | 9/1992  | Sundstrom |
|-----------|---|---|---------|-----------|
| 5,667,810 | A |   | 9/1997  | Levin |
| 5,807,295 | A | * | 9/1998  | Hutcheon et al. ............ 602/42 |
| 5,876,730 | A |   | 3/1999  | Brigstock et al. |
| 5,902,798 | A |   | 5/1999  | Gouda et al. |
| 5,906,828 | A | * | 5/1999  | Cima et al. ................. 424/423 |
| 5,955,588 | A |   | 9/1999  | Tsang et al. |
| 6,245,753 | B1| * | 6/2001  | Byun et al. .................. 514/56 |
| 6,342,591 | B1|   | 1/2002  | Zamora et al. |
| 6,486,140 | B2|   | 11/2002 | Hansson et al. |
| 2001/0038862 | A1 | 11/2001 | Luo et al. |
| 2001/0053839 | A1 | 12/2001 | Noishiki et al. |
| 2001/0056079 | A1 | 12/2001 | Hansson et al. |
| 2002/0018813 | A1 | 2/2002  | Burns et al. |
| 2002/0048563 | A1 | 4/2002  | Baetge et al. |
| 2002/0064551 | A1 | 5/2002  | Edwards et al. |
| 2002/0064559 | A1 | 5/2003  | Lee et al. |

FOREIGN PATENT DOCUMENTS

| WO | WO 92/13553 | 8/1992 |
| WO | WO 02/10221 | 2/2002 |

OTHER PUBLICATIONS

Ishihara M, Saito Y, Yura H, Ono K, Ishikawa K, Hattori H, Akaike T, Kurita D.J: Heparin-carrying polystyrene to mediate cellular attachment and growth via interaction with growth factors. Biomed Mater Res May; 50(2): 144-52 (2000).

Cox, M.D., David A., et al., "Effect of Local Delivery of Heparin and Methotrexate on Neointimal Proliferation in Stented Procine Coronary Arteries", *Coronary Artery Disease, Current Science*, vol. 3, (1992),237-248.

Edelman, Elazer R., et al., "Basic Fibroblast Growth Factor Enhances the Coupling of Intimal Hyperplasia and Proliferation of Vasa Vasorum in Injured Rat Arteries", *J. Clin. Invest.*, vol. 89, (Feb. 1992),465-473.

Ksander, George A., et al., "Exogenous Transforming Growth Factor-Beta 2 Enhances Connective Tissue formation and Wound Strength in Guinea Pig Dermal Wounds Healing by Secondary Intent", *Ann. Surg.*, (Mar. 1990),288-294.

Sellke, Frank W., "Therapeutic Angiogenesis with Basic Fibroblast Growth Factor: Technique and Early Results", *Ann. Thorac Surg 1998:65:1540-4*, (1988), 1540-1544.

\* cited by examiner

*Primary Examiner*—Leigh C. Maier
(74) *Attorney, Agent, or Firm*—Stephen A. Slusher; Janeen Vilven; Peacock Myers, P.C.

(57) ABSTRACT

A wound dressing, method of making, and method of use, utilizing a polymeric film having complexed thereto by hydrophobic interaction a construct including a polyanion covalently bonded to a hydrophobic prosthetic moiety, with one or more bioactive molecules directly complexed to the polyanion. The polyanion may be heparin or a heparin-activity molecule. The prosthetic group may include a hydrophobic silyl-containing moiety. Bioactive molecules include adhesive molecules, growth factor molecules, and therapeutic molecules, including antibiotics.

20 Claims, 7 Drawing Sheets

SEQUENCE LISTING

```
<160> NUMBER OF SEQ ID NOS: 4

<210> SEQ ID NO 1
<211> LENGTH: 28
<212> TYPE: PRT
<213> ORGANISM: Artificial
<220> FEATURE:
<223> OTHER INFORMATION: Synthetic FGF-2 analog

<400> SEQUENCE: 1

Asn Arg Phe His Ser Trp Asp Cys Ile Lys Thr Trp Ala Ser Asp Thr
1               5                   10                  15

Phe Val Leu Val Cys Tyr Asp Asp Gly Ser Glu Ala
            20                  25

<210> SEQ ID NO 2
<211> LENGTH: 10
<212> TYPE: PRT
<213> ORGANISM: Artificial
<220> FEATURE:
<223> OTHER INFORMATION: Heparin binding domain

<400> SEQUENCE: 2

Arg Lys Arg Lys Leu Glu Arg Ala Ile Arg
1               5                   10

<210> SEQ ID NO 3
<211> LENGTH: 5
<212> TYPE: PRT
<213> ORGANISM: Artificial
<220> FEATURE:
```

```
-continued

<223> OTHER INFORMATION: Laminin basement membrane derived protein

<400> SEQUENCE: 3

Ile Lys Val Ala Val
1               5

<210> SEQ ID NO 4
<211> LENGTH: 5
<212> TYPE: PRT
<213> ORGANISM: Artificial
<220> FEATURE:
<223> OTHER INFORMATION: Laminin basement membrane derived protein

<400> SEQUENCE: 4

Tyr Ile Gly Ser Arg
1               5
```

BIOACTIVE MEDICAL FILMS

CROSS-REFERENCE TO RELATED APPLICATIONS

This application is a continuation-in-part application of U.S. patent application Ser. No. 10/450,309, entitled "Bioactive Coating Compositions and Methods", to Paul O. Zamora, et al., filed on Jan. 28, 2003 now U.S. Pat No. 6,921,811, and the specification thereof is incorporated herein by reference.

This application claims the benefit of the filing of U.S. Provisional Patent Application Ser. No. 60/418,127, entitled "Bioactive Medical Films", filed on Oct. 10, 2002, and the specification thereof is incorporated herein by reference.

This application also claims priority to U.S. Pat. No. 6,342,591, entitled "Amphipathic Coating for Modulating Cellular Adhesion Composition and Methods", to Paul O. Zamora, et al., issued on Jan. 29, 2002, and the specification thereof is incorporated herein by reference.

BACKGROUND OF THE INVENTION

1. Field of the Invention (Technical Field)

The present invention relates to bioactive films, particularly film dressings for treatment of wounds, lesions and the like, which films include one or more bioactive molecules or medically useful substances bound to a hydrophobic group-containing polyanionic coating on the film.

2. Background Art

Treatment of various lesions, including ulcers, wounds and the like, is a medical challenge. Particularly in patients with compromised immune systems or disorders such as diabetes, ulcers, or sores, wounds and the like are extremely difficult to heal. It has been recognized that certain compounds that are locally delivered, such as cytokines, various drugs and the like, can aid in wound healing. However, there is no wound dressing or film which is effective in delivering these compounds over clinically relevant times. There are also no biodegradable wound dressings which, when applied to an internal injury such as to an organ or bone, deliver compounds over clinically relevant times.

It has previously been shown that various compounds useful for wound healing can bind to a number of different substrates. For example, growth factors can bind to polymer matrices and be later released. Growth factors combined with "matrix material" such as alginates, heparin, and so on, can bind to a paste which is useful for wound healing. Chitosan with an attached polysaccharide such as heparin, can also be used to make a film that is useful for wound healing.

Wound dressings that contain a drug useful for wound healing are known in the art. For example, the use of protease inhibitors in wound dressings has previously been shown. The peptide may either be attached directly to the dressing material or to a matrix. Another dressing for wounds uses corpuscles of a water-insoluble matrix that contains biologically active compounds. The corpuscles are attached to the wound dressing. However, there is no disclosure wherein these wound dressings allow for modulation of release of the compound. Finally, the use of cytokines and growth factors that bind to heparin and can be used on bandages has been shown. However, there is no disclosure of heparin binding to the bandage substrate, or modulation of release therefrom.

Use of coatings incorporating siloxanes is also known in the art, as is disclosed in U.S. Pat. No. 6,342,591, entitled Amphipathic Coating For Modulating Cellular Adhesion Composition and Methods, to Paul O. Zamora, Shigemasa Osaki and Ray Tsang; U.S. Pat. No. 5,955,588, entitled Non-Thrombogenic Coating Compositions and Methods for Using Same, to Ray Tsang and Shigemasa Osaki; and international patent application PCT/US01/24000, entitled Bioactive Coating Compositions and Methods, to Paul O. Zamora, Shigemasa Osaki and Ray Tsang. The specification of each of the foregoing is incorporated herein by reference.

There is thus a need for localized delivery of drugs, including biomolecules, for use in treatment of ulcers, sores, wounds and the like. For many conditions there is a need for controlled or sustained release over a period of time, such that the drug may be continuously delivered.

BRIEF SUMMARY OF THE INVENTION

In one embodiment, the invention provides a wound dressing including a polymeric film with a polyanion construct complexed to it by hydrophobic interaction. The polyanion construct includes a polyanion that is covalently bonded to a hydrophobic prosthetic moiety, and a first bioactive molecule complexed directly to the polyanion. The hydrophobic prosthetic moiety can include a linear repeat dimethylsilane group, a benzyl or a phenyl group covalently bound to at least one dimethylsilane group, styrene, cholesterol, a sterol, a fatty acid, an alkyl chain, or a phospholipid. The polyanion can include a heparin-activity molecule, collagen, a negatively charged chitosan derivative, polyacrylic acid, a chemically-modified dextan, a sulfated polysaccharide, sodium alginate or albumin. In another embodiment, a second bioactive molecule is complexed to the polyanion. In a preferred embodiment the second bioactive molecule is an antibiotic.

The invention further provides a wound dressing including a polymeric film with a molecule of Formula I complexed to it by hydrophobic interaction:

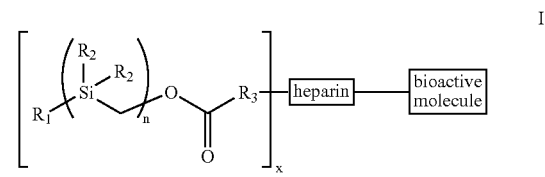

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, n is a number from 1 to 10, x is a number from 1 to about 30, and heparin is a heparin-activity molecule bonded to $R_3$ via a covalent bond, thereby forming a silyl-heparin covalent complex, with a first bioactive molecule directly complexed to the heparin-activity molecule.

In one embodiment of the invention of Formula I, the silyl-heparin covalent complex has a dissociation rate from the polymeric film determined by the value of n and x. In a preferred embodiment, the molecule of Formula I has an n value of 4 and an x value of 4. In another preferred embodiment, the molecule of Formula I has an n value of 2 and an x value of 6.

The silyl-heparin covalent complex of Formula I can be [benzyl-bis(dimethylsilylmethyl)]-(N-heparinyl)-carbamate or [benzyl-tris(dimethylsilylmethyl)]-(N-heparinyl)-carbamate.

The heparin-activity molecule can include heparin, heparan sulfate, hyaluronic acid, dextran, dextran sulfate, chondroitin sulfate, dermatan sulfate, a molecule including a mixture of variably sulfated polysaccharide chains composed of repeating units of D-glucosamine and either L-iduronic or D-glucronic acids, salts of any of the foregoing, derivatives of any of the foregoing, or combinations of any of the foregoing.

The bioactive molecule can include an adhesive molecule, a growth factor molecule, or a therapeutic molecule. The adhesive molecule can be collagen, fibronectin, laminin, vitronectin, thrombospondin, gelatin, polylysine, polyornithine, a peptide polymer containing at least one adhesive sequence and at least one heparin binding sequence, a sulfated complex carbohydrate, dextran sulfate, a growth hormone, a cytokine, a lectin, or peptidic polymers thereof. The growth factor molecule can be a fibroblast growth factor, platelet-derived growth factor, vascular endothelial growth factor, hepatocyte growth factor, placental growth factor, insulin-like growth factor, nerve growth factor, a neurotrophin, heparin-binding epidermal growth factor, transforming growth factorβ, bone morphogenetic protein 2, osteogenic protein 1 or keratinocyte growth factor. The therapeutic molecule can be C—X—C chemokine, interferon gamma, macrophage inflammatory protein-1, an interleukin, IL-1, IL-2, IL-3, IL-4, IL-6, IL-7, IL-8, interferon-gamma inducible protein-10, RANTES, an HIV-tat-transactivating factor, granulocye/macrophage-colony stimulating factor, platelet factor-4 (PF-4), endostatin, angiostatin, amino glycoside antibiotic, streptomycin, gentimicin, tobramycin, neomycin B, actinomycin D, daunorubicin, doxorubicin, bleomycin, rapamycin or paclitaxol.

The polymeric film can be a synthetic film such as polyurethane, poly tetrafluoroethylene, extended poly tetrafluoroethylene, copolyester, ethyl vinyl acetate, polyether block amides, polycaprolactone, polylactide, polyglycolide, or cellulose derivative. In a preferred embodiment the polymeric film is ethyl vinyl acetate. In another preferred embodiment, the polymeric film is a biodegradable polymeric film.

In a further embodiment, the wound dressing can include an absorbent layer in contact with one side of the polymeric film, with the construct comprising a polyanion covalently complexed to a hydrophobic prosthetic moiety, with a bioactive molecule directly bonded to the heparin activity molecule, complexed to the obverse side of the polymeric film. In a preferred embodiment the absorbent layer includes cotton, agar, chitosan, or a combination thereof. The polymeric film can further be permeable or impermeable to fluids.

In another embodiment, the invention provides a method for making a wound dressing by providing a wound contacting polymeric film, providing a molecule of Formula II:

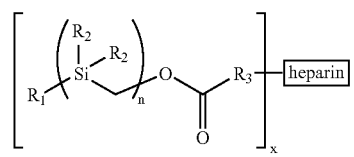

wherein $R_1$ is an $C_{1-8}$ alkyl or $C_{6-32}$ aryl group, each $R_2$ is independently selected from the group consisting of $C_{1-18}$ alkyl and $C_{6-32}$ aryl, $R_3$ is N or O, n is a number from 1 to 10, and heparin is a heparin-activity molecule bound to the silyl moiety via covalent bonding, wherein x is from 1 to about 30 for each heparin-activity molecule, thereby forming a silyl-heparin complex, attaching the silyl-heparin complex of Formula II to the polymeric film by hydrophobic interaction, and attaching a first bioactive molecule to the heparin-activity molecule. In Formula II, the silyl-heparin covalent complex has a dissociation rate from the polymeric film determined by the value of n and x. A second bioactive molecule can be attached to the heparin-activity molecule of Formula II. In a preferred embodiment the second bioactive molecule is an antibiotic.

The invention further provides a method of treating a wound by providing the wound dressing as described and contacting the dressing to the wound. The wound is a surface lesion or an internal wound. In a preferred embodiment, applicable particularly where the wound is an internal wound, the wound dressing can include a biodegradable polymeric film. The wound dressing can include a first bioactive molecule that is an adhesive molecule, whereby the contacting surface is non-thrombogenic and promotes cellular adhesion.

A primary object of the invention is to provide a coating composition for contacting surfaces of bandages and other wound-contacting medical films, wherein the composition comprises a silyl-heparin-bioactive molecule complex, attached to the contacting surface by hydrophobic interaction.

A further object of the invention is to provide an amphipathic silyl-heparin-fibronectin coating composition for contacting surfaces of bandages and other wound-contacting medical films, which promotes cellular attachment.

A further object of the invention is to provide a coating the composition of which can be varied, such that in one embodiment the invention provides a silyl-heparin-growth factor molecule composition, and in another embodiment the invention provides a silyl-heparin-therapeutic molecule composition.

A further object of the invention is to provide a polymeric film with a coating including a polyanion with a hydrophobic prosthetic moiety covalently bound thereto, with a bioactive molecule complexed to the polyanion.

A further object of the invention is to provide a cost effective and commercially feasible method for coating polymeric bandages and other wound-contacting medical films, including biodegradable bandages and films, with a coating comprising a bioactive molecule.

A further object of the present invention is to provide a cost effective and commercially feasible method for coating bandages and other wound-contacting medical films, including biodegradable bandages and films, with a coating comprising a silyl-heparin-bioactive molecule composition.

A primary advantage of the present invention is that it provides for coating contacting surfaces of bandages and other wound-contacting medical films with a durable and low-cost coating that promotes the desired biological or therapeutic effect, depending on the bioactive molecule selected.

Another advantage of the present invention is that it provides a method for determining the dissociation rate of silyl-heparin-bioactive molecule complexes from contacting surfaces by, in part, determining the number of silyl units per silyl moiety, or the number of silyl moieties per heparin molecule, or both.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DESCRIPTION OF THE PREFERRED EMBODIMENTS

BEST MODES FOR CARRYING OUT THE INVENTION

Figure 1:
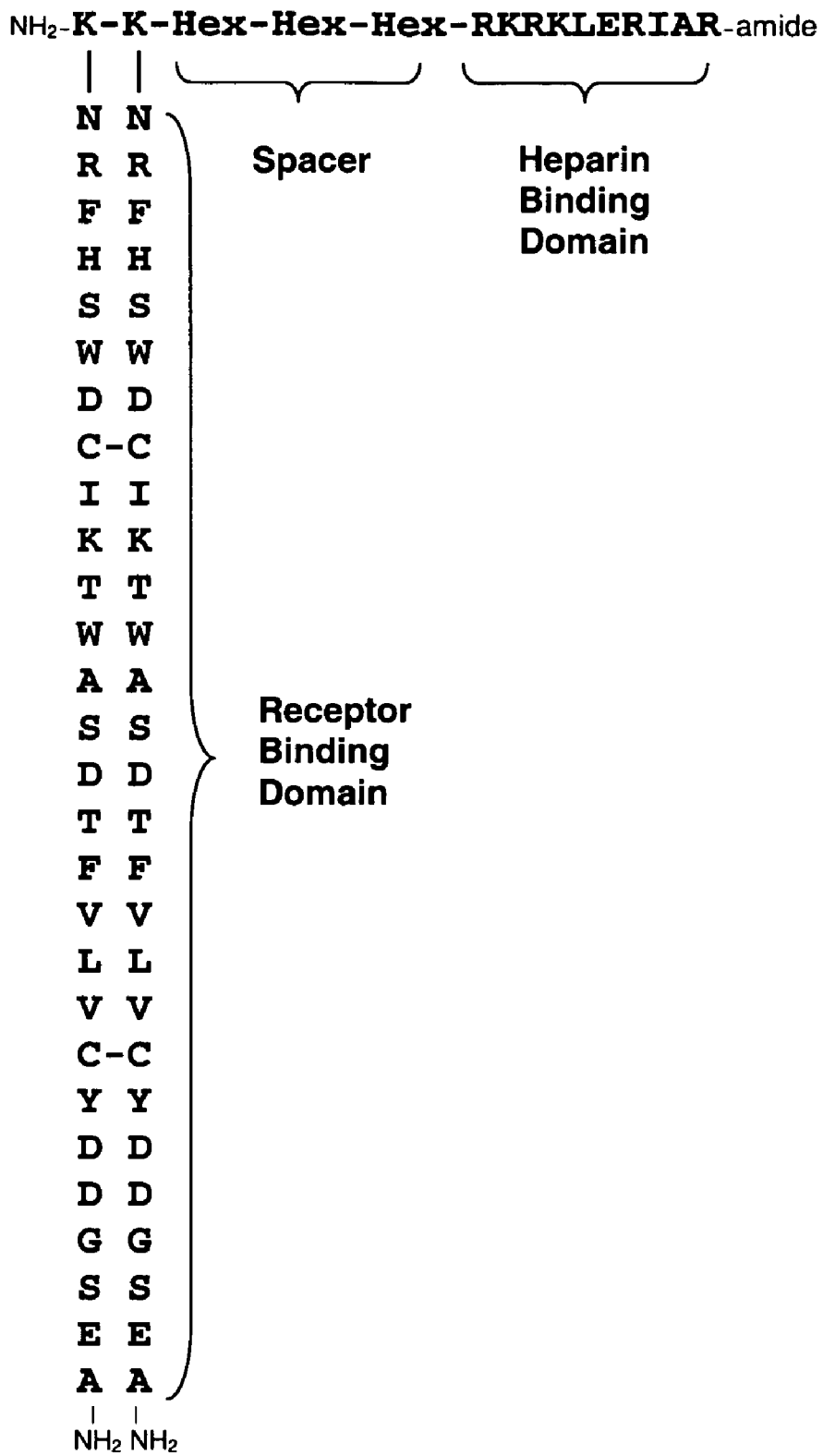
FIG. 1 shows the structure of the synthetic FGF-2 peptide analog, F2A3. The amino acid sequence of the receptor binding domains, NRFHSWDCIKTWASDTFVLVCY-DDGSEA (SEQ ID NO:1), are covalently linked by amide bonds to a lysine residue. The second lysine residue is bonded by means of a covalent peptide bond to one terminus of a tripeptide formed from three aminohexanoic acid residues. The opposite terminus of the aminohexanoic acid tripeptide is covalently bonded by a peptide bond to heparin-binding peptide RKRKLERAIR (SEQ ID NO:2).

The invention provides a bioactive, coated film dressing for the topical treatment of tissue wounds and lesions, especially those of the skin. The dressing includes:
a) a polymeric film,
b) a molecular coating composed of an adsorbable polyanion, and
c) a bioactive molecule complexed to the adsorbable polyion.

The film is composed of one or more layers and may be made of polyurethane, poly tetrafluoroethylene, extended poly tetrafluoroethylene, copolyesters, ethyl vinyl acetate, polyether block amides, polycaprolactone, polylactide, polyglycolide, cellulose derivatives, combinations of the aforementioned, or the like. In a preferred embodiment the film is made of ethyl vinyl acetate. The film may be thin and be intended to conform to the application site (conformal) or be adhered to a support structure such as a bandage or compress. The film may be occlusive and non-breathable, or preferably be capable of allowing water transit (breathable). A breathable film may be a perforated sheet, such as perforated ethyl vinyl acetate, or may be a woven material, such as a woven polymeric film or a woven cotton film. The thickness of the film(s) can vary, such as from about 0.5 mil to about 10 mils. In a preferred embodiment the film is between about 1 and about 2 mils thick.

The film is coated with an adsorbable polyanion. The adsorbable polyanion may be any polyanion to which has been conjugated a prosthetic unit intended to increase the hydrophobicity of the polyion. The polyanion may include heparin, hyaluronic acid, chondroitin sulfate, dextran, amino-dextran, dextran sulfate, or modifications of the foregoing such as DEAE-dextran, CM-dextran or the like. In a preferred embodiment the polyanion includes heparin. The prosthetic unit may be an alkyl chain, a linear unit containing a benzyl or phenyl group plus at least one dimethylsilane group, or any other prosthetic unit intended to increase the adsorption of the conjugated polyanion to the film. In a preferred embodiment the prosthetic group is composed of linear units containing benzyl-dimethylsilane.

The "bioactive molecule" is a medically useful substance that binds the adsorbable heparin. The bioactive molecule may be a molecule intended to increase cell attachment, to modulate biological activity, or to inhibit infections. Examples of molecules intended to increase cell attachment include any of the various types of collagen (type I, type IV, etc.), laminin, fibronectin, fibrinogen, elastin, or amino acid polymers that bind to heparin and support cell attachment. Examples of molecules that modulate biological activity include heparin-binding growth factors and peptides and analogs derived therefrom, synthetic growth factors, chemokines and modulators of the immune system, and modulators of angiogenesis. Specific examples include any of the known fibroblast growth factors (FGF-1 to FGF-23), the synthetic fibroblast growth factor F2A3, HBBM (heparin-binding brain mitogen), HB-GAF (heparin-binding growth associated factor), HB-EGF (heparin-binding EGF-like factor) HB-GAM (heparin-binding growth associated molecule, also known as pleiotrophin, PTN, HARP), TGF-α (transforming growth factor-α), TGF-βs (transforming growth factor-βs), VEGF (vascular endothelial growth factor), EGF (epidermal growth factor), IGF-1 (insulin-like growth factor-1), IGF-2 (insulin-like growth factor-2), PDGF (platelet derived growth factor), RANTES, SDF-1, secreted frizzled-related protein-1 (SFRP-1), small inducible cytokine A3 (SCYA3), inducible cytokine subfamily A member 20 (SCYA20), inducible cytokine subfamily B member 14 (SCYB14), inducible cytokine subfamily D member 1 (SCYD1), stromal cell-derived factor-1 (SDF-1), thrombospondins 1, 2, 3 and 4 (THBS1-4), platelet factor 4 (PF4), lens epithelium-derived growth factor (LEDGF), midikine (MK), macrophage inflammatory protein (MIP-1), moesin (MSN), hepatocyte growth factor (HGF, also called SF), placental growth factor, IL-1 (interleukin-1), IL-2 (interleukin-2), IL-3 (interleukin-3), IL-6 (interleukin-6), IL-7 (interleukin-7), IL-10 (interleukin-10), IL-12 (interleukin-12), IFN-α (interferon-α), IFN-γ(interferon-γ), TNF-α (tumor necrosis factor-α), SDGF (Schwannoma-derived growth factor), nerve growth factor, neurite growth-promoting factor 2 (NEGF2), neurotrophin, BMP-2 (bone morphogenic protein 2), OP-1 (osteogenic protein 1, also called BMP-7), keratinocyte growth factor (KGF), interferon-γ inducible protein-20, and HIV-tat-transactivating factor, amphiregulin (AREG), angio-associated migratory cell protein (AAMP), angiostatin, betacellulin (BTC), connective tissue growth factor (CTGF), cysteine-rich angiogenic inducer 61 (CYCR61), endostatin, fractalkine/neuroactin, or glial derived neurotrophic factor (GDNF), GRO2, hepatoma-derived growth factor (HDGF), granulocyte-macrophage colony stimulating factor (GMCSF), C—X—C chemokines, C—X—C chemokines lacking the ELR motif (ELR—C—X—C chemokines), endostatin, angiostatin, and peptide analogs or mimetics thereof, and the many growth factors, cytokines, interleukins and chemokines that have an affinity for heparin. Examples of molecules intended to inhibit infections include amino glycoside antibiotics such as gentimicin, tobramycin and neomycin, and other antibiotics that carry charge groups.

The bioactive, coated films of this invention may be used to treat full-thickness wounds, abrasions, chronic wounds, diabetic ulcers, pressure ulcers, venous stasis (circulatory) ulcers, infections, cuts, incisions, burns, or other surface lesions arising from trauma or disease. In addition to surface lesions, the bioactive, coated films may be used internally, such as over soft tissue lesions, organ injuries, around bone, teeth, cartilage or other structures, and as packing material for deep tissue wounds. A "wound" as used herein includes any of the foregoing. For use internally, it is preferred to use a biodegradable film, such as for example, a polycaprolactone or polylactide. One particularly attractive clinical application is the treatment of lower extremity diabetic neuropathic ulcers that extend into the subcutaneous tissue or beyond and have an adequate blood supply. In the case of treatment of ulcers, the film of this invention can be used as an adjunct to ulcer care, and employed following initial debridement, pressure relief, and infection control.

In a preferred embodiment, the bioactive, coated film is made of ethyl vinyl acetate and is coated with silyl-heparin of a molecular weight averaging 12,000 Daltons. Silyl-heparin containing an average of at least about four hydrophobic silyl prosthetic units is used to provide adsorptive character. The prosthetic units are covalently conjugated to the heparin. The bioactive molecule is recombinant fibroblast growth factor-2 (FGF-2). In another preferred embodiment the bioactive molecule is the synthetic FGF-2 analog designated F2A3. In the case of F2A3, the film will have biological activity similar to FGF-2, which includes promoting the chemotactic recruitment and proliferation of cells involved in wound repair and enhancing the formation of granulation tissue. The teaching of U.S. patent application Ser. No. 10/224,268, disclosing F2A3 and related peptides, is incorporated herein by reference.

The adsorbable polyanion and the bioactive molecule may be applied to the film serially or in combination, but preferably serially, and can be applied by immersion, spraying, painting, or the like. In a preferred embodiment, the films can be immersed in an aqueous solution of 60% isopropanol (v/v) containing 0.25% silyl-heparin (w/v) for 15 minutes at 37° C. Unbound material is then rinsed with water and the films air-dried at 56° C. The films with adsorbed silyl-heparin are then immersed in phosphate buffered saline containing 100 ng/mL of a bioactive molecule, such as for example F2A3, for 30 minutes at 37° C. and air-dried. The films are then place in foil pouches and sealed. The films may be prepared to be aseptic with low bioburden or be sterile.

Film may be perforated to improve permeability, or allow transit of gases and fluids, and the like. In one embodiment the film is about 0.5 to 10 mils thick, and preferably about 1 to 2 mils thick. The transit of moisture measured as the moisture vapor transfer rate (MVTR) can be from 0-10,000 g/cm²/24 hours, and preferably below 2500 g/cm²/24 hours. The film may be composed of Saran®, Saran HB®, Saranex®, ACLAR®, polyester, metallized polyester, nylon, metallized nylon, polyvinylidene fluoride copolymer (PVDC), PVDC-Nylon, PVDC-coated polyester, polyvinylchloride, polycarbonate, polystyrene, polyethylene, polyurethane, copolyesters, ethyl vinyl acetate, polyether block amides, poly tetrafluoroethylene, or biodegradable films composed of polycaprolactone, polylactide, or the like.

The present invention includes bioactive coating compositions comprising a silyl-heparin-bioactive molecule complex, methods for making and using the same, and bandages and medical films including the same. In one embodiment, the silyl-heparin-bioactive molecule complex comprises a complex of Formula I:

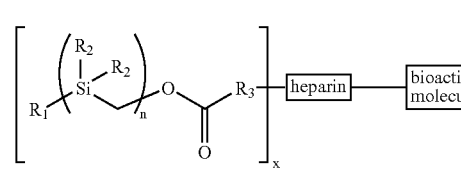

I wherein $R_1$ is an $C_{1-20}$ alkyl or $C_{6-32}$ aryl group, each $R_2$ is independently selected from the group consisting of $C_{1-20}$ alkyl and $C_{6-32}$ aryl, $R_3$ is N or O, and n is a number from 1 to 10. X is from 1 to about 30, such that from 1 to about 30 silyl moieties are covalently bonded to a heparin molecule. One or more bioactive molecules, which may be the same or different, are complexed to the heparin molecule.

In one embodiment, the present invention provides bioactive molecules that are adhesive molecules, thereby forming an amphipathic coating that promotes cell attachment. In another embodiment, the present invention provides bioactive molecules that are growth factors molecules, thereby forming a coating providing for regional or localized delivery of the growth factor molecules. In yet another embodiment, the present invention provides bioactive molecules that are therapeutic molecules, thereby forming a coating providing for regional or localized delivery of the therapeutic molecules.

In another embodiment, the present invention provides wound-contacting medical devices with the contacting surface thereof coated with moieties of the foregoing formula, which moieties are covalently bonded to a hydrophobic prosthetic unit and heparin molecule complex, with one or more bioactive molecules complexed to the heparin molecule.

Unless otherwise defined, all technical and scientific terms employed herein have their conventional meaning in the art. As used herein, the following terms have the meanings ascribed to them.

"Alkyl" refers to linear branched or cyclic, saturated or unsaturated $C_{1-20}$ hydrocarbons such as methyl, ethyl, ethenyl, propyl, propenyl, iso-propyl, butyl, iso-butyl, t-butyl, pentyl, cyclopentyl, hexyl, cyclohexyl, octyl, dodectyl, and the like.

"Aryl" refers to unsaturated $C_{6-32}$ hydrocarbon rings that may be substituted from 1-5 times with alkyl, halo, or other aryl groups. Aryl also includes bicyclic aryl groups. Specific examples of aryl groups include but are not limited to phenyl, benzyl, dimethyl phenyl, tolyl, methyl benzyl, dimethyl benzyl, trimethyl phenyl, ethyl phenyl, ethyl benzyl, and the like.

"Adhesive molecule" refers to bioactive molecules which promote cellular attachment, adhesion or growth, including fibronectin, laminin, vitronectin, thrombospondin, heparin-binding domains, and heparan sulfate binding domains, as well as synthetic polymers of amino acids containing adhesive sequences derived from any of the foregoing. This includes, without limitation, peptides or polypeptides containing the amino acids with the single letter codes RGD, IKVAV (SEQ ID NO:3), YIGSR (SEQ ID NO:4), and the like. Adhesive molecules also include lectins that bind to heparin and carbohydrate moieties on cell surfaces.

"Bioactive molecule" refers to any molecule with biological activity within the body, including molecules used as a drug, to effect a biochemical change in an organism, or to confer a benefit to an organism as defined above. The bioactive molecule preferably binds to one or more forms of heparin. A bioactive molecule includes an adhesive molecule, a growth factor molecule or a therapeutic molecule as disclosed herein. A bioactive molecule further includes art conventional drugs, compounds, molecules, peptides, peptidomimetics, antibodies and fragments and mimics thereof, and the like. A bioactive molecule may, but need not, bind to a receptor in the organism, be a receptor for an endogenous substance found in an organism, or be an agonist, antagonist, or a mixed agonist-antagonist of a receptor-mediated process or reaction. In a preferred embodiment, the bioactive molecule may be bonded to heparin by any means known in the art, including but not limited to affinity binding.

"Growth factor molecule" refers to a bioactive molecule that is a growth factor, mimic of a growth factor, derivative of a growth factor, or other molecule that has the effect of a growth factor. This includes fibroblast growth factor, platelet-derived growth factor, vascular endothelial growth factor, hepatocyte growth factor, placental growth factor, insulin-like growth factor, nerve growth factors and neurotrophins, heparin-binding epidermal growth factor, transforming growth factor-β, bone morphogenetic protein 2 (BMP-2), osteogenic protein 1 (OP-1, also called BMP-7) and keratinocyte growth factor. It further includes peptides, peptidomimetics and other molecules, whether made by synthetic means, recombinant means or otherwise, which have the biological activity of a growth factor, including without limitation any of the foregoing. For example, it also includes synthetic growth factor molecules such as the FGF peptide analog F2A3, the structure of which is shown in FIG. 1. F2A3 and other synthetic growth factor molecules that may be employed in this invention are further described in U.S. patent application Ser. No. 10/224,268, entitled Synthetic Heparin-Binding Growth Factor Analogs, and the specification thereof is incorporated herein by reference. In a preferred embodiment, the bioactive molecule may be bonded to heparin by any means known in the art, including but not limited to affinity binding.

"Heparin" as used herein includes complex carbohydrates or mimetics of complex carbohydrates with properties similar to those of heparin, including heparan sulfate, hyaluronic acid, dextran, dextran sulfate, chondroitin sulfate, dermatan sulfate, and the like, including but not limited to a molecules including a mixture of variably sulfated polysaccharide chains composed of repeating units of D-glucosamine and either L-iduronic or D-glucuronic acids, derivatives of any of the foregoing and salts of any of the foregoing. Heparin derivatives include, but are not limited to ammonium heparin, benzalkonium heparin, and the like. Conventional salts of heparin include sodium heparin, calcium heparin, magnesium heparin, and potassium heparin. Sodium heparin is a preferred form of heparin for preparing the covalent complexes according to the present invention. Any suitable form of heparin may be employed in the reaction.

"Therapeutic molecule" refers to any molecule having a therapeutic effect, such as a chemokine, hormone, angiogenesis inhibitor or drug, and particularly a therapeutic molecule intended for local or regional delivery within the body over a sustained period. Examples of chemokines and modulators of the immune system include C—X—C chemokines, interferon gamma, macrophage inflammatory protein-1, interleukins including IL-1, IL-2, IL-3, IL-4, IL-6, IL-7 and IL-8, interferon-gamma inducible protein-10, RANTES, HIV-tat-transactivating factors, and granulocye/macrophage-colony stimulating factor. Examples of angiogenesis inhibitors include platelet factor-4 (PF-4), C—X—C chemokines lacking the ELR motif (ELR—C—X—C chemokines), endostatin and angiostatin. Examples of drugs include amino glycoside antibiotics, including streptomycin, gentimicin and neomycin B; and anti-cancer antibiotics, including actinomycin D, daunorubicin, doxorubicin, bleomycin, rapamycin and paclitaxol. In a preferred embodiment, the therapeutic molecule may be complexed or bonded to heparin by any means known in the art, including but not limited to affinity binding.

In the following discussion and examples, "µL" means microliter, "mL" means milliliter; "mil" means a unit of measure equal to $10^{-3}$ inches, "L" means liter, "µg" means microgram, "mg" means milligram, "g" means gram, "cm" means centimeter, "mol" means moles, "M" means molar concentration, "Me" means methyl; "Bn" means benzyl, "nBu$_4$NI" means tetrabutyl-ammonium iodide, "° C." means degrees Centigrade. All percentages are in percent by weight unless otherwise indicated.

The silyl moiety is represented by Formula I wherein $R_1$ is an $C_{1-20}$ alkyl or $C_{6-32}$ aryl group, each $R_2$ is independently selected from the group consisting of $C_{1-20}$ alkyl and $C_{6-32}$ aryl, $R_3$ is N or O, and n is a number from 1 to 10. As will be apparent to those skilled in the art, $R_3$ is an N or O atom in the heparin molecule, and the unoccupied bond from $R_3$ signifies the attachment of the silyl moiety to the heparin molecule. Thus, the hydrophobic silyl moiety is capable of attachment to the heparin molecule at either an O atom of an alcohol (i.e., hydroxyl) or an N atom of an amine.

Heparin comprises many repeating units containing amine and hydroxyl functional groups which can be the site for attachment of the hydrophobic silyl moiety to the heparin molecule. Accordingly, one embodiment of the present invention contemplates the attachment of more than 1 hydrophobic silyl moiety to a single heparin molecule. As many as 30 or more hydrophobic silyl moieties as shown in Formula I, and as few as 1 hydrophobic silyl moiety, may be attached to a single heparin molecule to achieve the covalent complex employed in the heparin coating compositions of the present invention. In one embodiment of the present invention, between 2 and 25 hydrophobic silyl moieties are attached to a single heparin molecule. In another embodiment, between 5 and 20 hydrophobic silyl moieties are attached to a single heparin molecule. In another embodiment, between 7 and 15 hydrophobic silyl moieties are attached to a single heparin molecule. In a preferred embodiment, 7 or 8 hydrophobic silyl moieties are attached to a single heparin molecule. In another preferred embodiment 12 hydrophobic silyl moieties are attached to a single heparin molecule.

As disclosed herein, the silyl-heparin complex is bonded to the contacting surface of a medical device by means of hydrophobic interaction between the hydrophobic silyl moieties and the contacting surface, which is preferably also hydrophobic. The strength of the attachment, and the dissociation rate of silyl-heparin complexes from the contacting surface, is determined by at least three factors: the number of silyl units per silyl moiety (i.e., where n is a number between 1 and 10), the number of silyl moieties per single heparin molecule (i.e., where x is a number between 1 and about 30), and the degree of hydrophobicity of the contacting surface. For applications where minimal or functionally no dissociation is desired, such as certain applications with adhesive molecules bonded to the silyl-heparin complex, the number of silyl units per silyl moiety and the number of silyl moieties per heparin molecule may each be increased to the optimal number for maximal binding strength, and similarly the contacting surface may be selected so as to provide optimal hydrophobic binding with the silyl moieties. For applications where controlled release over time is desired, such as certain applications with growth factor or therapeutic molecules bonded to the silyl-heparin complex, fewer silyl units per silyl moiety or fewer silyl moieties per heparin molecule, or both, are selected, or a contacting surface providing decreased hydrophobic binding to the silyl moiety is selected, or a combination thereof, such that the desired release over time in vivo is obtained.

In those embodiments wherein more than one hydrophobic silyl moiety is attached to a single heparin molecule, the hydrophobic silyl moieties may be attached either through the amine of heparin (e.g., where $R_3$ is N) or through the hydroxyl group of heparin (e.g., wherein $R_3$ is O). In other words, some of the hydrophobic silyl moieties may be attached to the heparin molecule via bonding at the amine groups of heparin, while other hydrophobic silyl moieties are attached to the heparin molecule via bonding at the hydroxyl groups of heparin. It is also possible for all of the hydrophobic silyl moieties to be consistently attached to heparin via one or the other of the amine (e.g., $R_3$ in all hydrophobic silyl moieties is N) or the alcohol (e.g., $R_3$ in all hydrophobic silyl moieties is O).

The bonds between the hydrophobic silyl moieties and the heparin molecule that effect the attachment of the silyl moieties to the heparin molecule are covalent bonds. Thus, the coating compositions of the present invention do not rely upon ionic interactions between heparin and the hydrophobic moiety. Rather, the hydrophobic moieties are bonded to the heparin molecule by covalent bonding through either the amine or hydroxyl groups (or possibly a combination of both amine and hydroxyl groups, when two or more hydrophobic silyl moieties are attached to a single heparin molecule). Because the hydrophobic silyl moiety is bonded to the heparin molecule through covalent bonding, the present invention overcomes one weakness of conventionally known heparin coatings. Specifically, the problem of heparin leaching from the coating as a result of the breaking of the ionic bond between heparin and the group which attaches heparin to the surface is overcome by avoiding reliance upon ionic bonding interactions between heparin and the binding group. In the present invention, the covalent bonds between the hydrophobic silyl moieties and the heparin molecule in the coating composition are not disrupted by the presence of ionic species in the blood with which the coated surface will come into contact. The data demonstrate that this process of covalent modification also does not lead to detrimental loss of heparin activity as monitored by a Factor Xa/antithrombin III chromogenic substrate assay on the surface of target substrates.

The covalent complex according to the present invention can be prepared according to the following Scheme 1.

Scheme 1

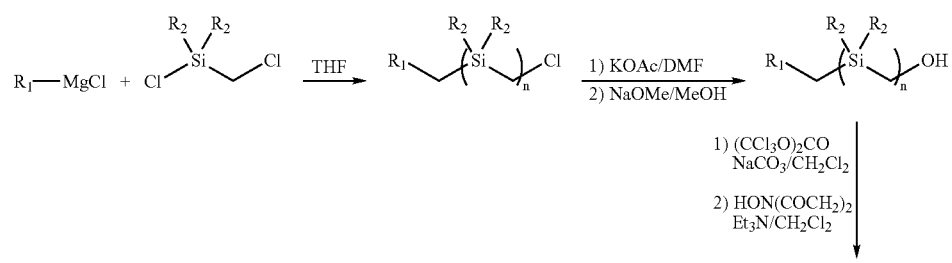

-continued

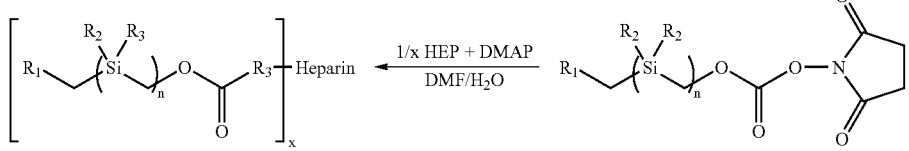

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O, n is a number from 1 to 10, and x is a number from 1 to about 30.

Generally, the first intermediate, $R_1(Si(R_2)_2CH_2)_nCl$, wherein n is 1, is produced by reacting an alkyl or aryl magnesium chloride with a chloro(chloromethyl)-dialkyl silane or chloro(chloromethyl)diaryl silane in the presence of tetrahydrofuran (THF). The alkyl or aryl magnesium chlorides used as starting materials are commercially available, and include, for example benzyl magnesium chloride. Chloro(chloromethyl)dialkyl silanes and chloro(chloromethyl)diaryl silanes are commercially available and include, for example chloro(chloromethyl)dimethyl silane. The reaction is exothermic, and is typically conducted at temperatures of about 10° C. or less. The reaction is carried out for a sufficient period of time to yield about 80-90% product. Typically the reaction is conducted over a period of from about 2 to about 24 hours.

First intermediates wherein n is 2 or higher can be produced using a Grignard reaction involving the reaction of the first intermediate wherein n is 1 with $ClSi(R_2)_2CH_2Cl$. This Grignard reaction can be repeated any number of times to achieve the desired value for n in the first intermediate. The reaction is carried out in the presence of a catalytic amount of iodine and THF.

The first intermediate (wherein n is 1-10) is converted to the second intermediate, $R_1(Si(R_2)_2CH_2)_nOH$, by reacting the first intermediate with potassium acetate (KOAc) in dimethyl formamide (DMF), at a temperature of above about 120° C., and preferably about 135° C., for between 12 and 24 hours. The product of this reaction is then reacted with sodium methoxide (NaOMe) in methanol (MeOH) under reflux for about 2 hours to achieve the second intermediate.

The second intermediate is converted to the last intermediate, $R_1(Si(R_2)_2CH_2)_nOCO_2N(COCH_2)_2$, by a two-step reaction process. In the first step, the second intermediate is reacted with triphosgene and sodium carbonate in methylene chloride at a temperature of less than 10° C., and preferably about 0° C. The product of this reaction is reacted with N-hydroxysuccinimide and triethylamine ($Et_3N$) in methylene chloride at a temperature of less than 10° C., and preferably about 0° C.

The final intermediate is covalently conjugated to heparin by reacting heparin with the final intermediate in a suitable solvent (e.g., water/dimethyl formamide) at a pH of about 8.0 to 9.0, and preferably about 8.5. The pH of the reaction is controlled by the addition of base such as sodium hydroxide, as needed. Alternatively and preferably, a slight excess of 4-dimethylaminopyridine (DMAP) can be used as base for the conjugation reaction with heparin. Using these general methods, the covalent silyl-heparin complexes of the present invention can be produced. The covalent complexes have general Formula II:

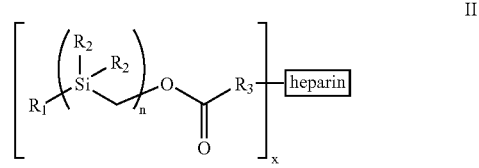

wherein $R_1$ is an $C_{1-18}$ alkyl or $C_{6-32}$ aryl group, each $R_2$ is independently selected from the group consisting of $C_{1-18}$ alkyl and $C_{6-32}$ aryl, $R_3$ is N or O of heparin, n is a number from 1 to 10, and x is a number from 1 to about 30.

Preferred complexes include those complexes wherein $R_1$ of the hydrophobic silyl moiety is aryl. In one preferred embodiment, $R_1$ is benzyl. In one preferred embodiment, each $R_2$ is alkyl. In another preferred embodiment, each $R_2$ is selected from the group consisting of methyl, ethyl, propyl, and isopropyl, particularly methyl. In one preferred embodiment, n is a number from 2 to 3.

In one particularly preferred embodiment the complex is a molecule of Formula III:

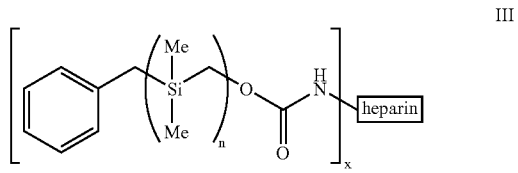

wherein n is a number from 1 to 10, and x is a number from 1 to about 30.

Specific examples of covalent complexes according to the present invention include but are not limited to [benzyl-bis(dimethylsilylmethyl)]-(N-heparinyl)-carbamate, [benzyl-tris(dimethylsilylmethyl)]-(N-heparinyl)-carbamate, and dodecyl[benzyl-bis(dimethylsilylmethyl)]-(N-heparinyl)-carbamate. Although these three specific covalent complexes are examples of currently preferred covalent complexes having the general Formula II above, other specific examples of such complexes will be apparent to those skilled in the art and are contemplated by the instant invention.

The silyl-heparin coatings of the present invention include the silyl-heparin covalent complexes described above. In addition to the silyl-heparin covalent complex, the coating composition may also include one or more solvents that facilitate the processes of applying the composition to the surface. Suitable solvents include those which at least partially solubilize the covalent complex and which do not interfere with the anti-thrombogenic activity of heparin. Examples of solvents which may be employed in the coating compositions of the present invention include but are not limited to aqueous solvents, alcohols, nitrites, amides, esters, ketones, ethers, and the like. "Aqueous", with reference to solutions or solvents, refers to solutions or solvents that consist primarily of water, normally greater than 90% water by weight, and includes essentially or substantially pure water. For example, an aqueous solution or solvent can be distilled water, tap water, or the like. However, an aqueous solution or solvent can also include water having substances such as pH buffers, pH adjusters, organic and inorganic salts, alcohols (e.g., ethanol), sugars, amino acids, or surfactants incorporated therein. The aqueous solution or solvent may also be a mixture of water and minor amounts of one or more co-solvents, including agronomically suitable organic co-solvents, which are miscible therewith, or may form an emulsion therewith. Examples of suitable alcohol solvents include but are not limited to methanol, ethanol, propanol, isopropanol, hexanol, as well as glycols such as ethylene glycol and the like. Examples of suitable nitriles include acetonitrile, propionitrile, butyronitrile, benzonitrile and the like. Examples of suitable amides include formamide, N,N-dimethylformamide, N,N-dimethylacetamide and the like. Examples of suitable esters include methyl acetate, ethyl acetate and the like. Examples of suitable ketones include acetone, methyl ethyl ketone, diethyl ketone and the like. Examples of suitable ethers include diethyl ether, tetrahydrofuran, dioxane, dimethoxyethane and the like. Any two or more of any of the foregoing solvents may be utilized in the coating composition as well. Currently preferred solvents include water, particularly distilled water, isopropanol, acetonitrile, and combinations of any two or more of these solvents.

In one preferred embodiment, the silyl-heparin covalent complex is solubilized in solvent to achieve a concentration of between about 0.01 and about 10 percent by weight, preferably between about 0.1 and about 1 percent, and more preferably about 0.125 percent.

In addition to the foregoing solvents, the silyl-heparin coating compositions of the present invention may also include therein various conventional additives. Examples of additives which may be incorporated into the compositions of the present invention include but are not limited to benzalkonium, 4-dimethylaminopyridinium, tetrabutylammonium halides, and the like.

Any of a number of heparin-related compositions is known and suitable for use in this invention. For example, Liu, J., A. Pervin, C. M. Gallo, U. R. Desai, C. L. Van Gorp, and R. J. Linhardt: New approaches for the preparation of hydrophobic heparin derivatives. *J Pharm Sci* 83:1034-9 (1994), discloses a heparin derivative sufficiently lipophilic to be bonded to plastics. Lipophilic substituents are attached to the reducing termini of heparin chains, resulting in enhanced hydrophobicities. In one method octyl isocyanate and octadecyl isocyanate were coupled to the core peptide of peptidoglycan heparin to form octyl- and octadecyl-peptidoglycan heparins, which were purified by hydrophobic interaction chromatography on phenyl-Sepharose CL-4B. In another method lipophilic acyl hydrazides of various long chain fatty acids were coupled to heparin's reducing end, with the stearic ($C_{18}$) hydrazide derivatives of heparin showing a measurable increase in lipophilicity. Alternatively, two lipophilic chains, lauryl ($C_{12}$) and stearyl ($C_{18}$) can be coupled to a single heparin chain, resulting in a heparin derivative having enhanced hydrophobicity.

In another example, Sasseen B M, Gray B D, Gal D, Lorinc R, Carpenter D C, Klugherz B D, Wilensky R L:Local delivery of a hydrophobic heparin reduces neointimal hyperplasia after balloon injury in rat carotid but not pig coronary arteries. *J Cardiovasc Pharmacol Ther* October;6 (4):377-83 (2001), discloses a hydrophobic heparin (PTIR-RS-1). Similarly, Ishihara M, Saito Y, Yura H, Ono K, Ishikawa K, Hattori H, Akaike T, Kurita A. J: Heparin-carrying polystyrene to mediate cellular attachment and growth via interaction with growth factors. *J Biomed Mater Res* May;50(2):144-52 (2000), discloses various sugar-carrying polystyrenes (PSs), which consist of synthetic styrene and sugar moieties, are glycoconjugates that are able to attach to polymeric surfaces, including heparin, thereby resulting in heparin-carrying PS (HCPS). HCPS is able to retain the binding of heparin-binding growth factors such as vascular endothelial growth factor or fibroblast growth factor.

INDUSTRIAL APPLICABILITY

The invention is further illustrated by the following non-limiting examples.

EXAMPLE 1

Synthesis of Adsorbable Heparin Based on Conjugation of Dodecyl Groups

Grignard Reaction of Dodecyl magnesium bromide and Chloro(chloromethyl)-dimethylsilane. Under a nitrogen atmosphere, $ClSiMe_2CH_2Cl$ was dissolved in tetrahydrofuran (THF) and then cooled in an ice/acetone bath. Dodecyl MgCl was then slowly introduced in a 1 M solution such that the temperature was maintained below 10° C. The reaction was allowed to proceed with stirring overnight, after which a white suspension was obtained. Saturated aqueous $NH_4Cl$ was added to quench the reaction. The reaction mixture was mixed with hexane and the mixture allowed to partition. The organic phase was removed by the addition of hexane and the 2 phases were shaken vigorously and partitioned. Residual water was removed from the organic phase with $MgSO_4$, and the reaction product dodecyldimethylsilylmethylchloride was concentrated under vacuum.

Acetolysis of Dodecyldimethylsilylmethylchloride. Dodecyldimethylsilylmethylchloride was dissolved in dimethylformamide and KOAc was added followed addition of $nBu_4NI$. The suspension was heated to 120° C. and allowed to react to completion. The reaction mixture was cooled and quenched with by adding an aliquot of a saturated aqueous NaCl solution. The reaction product was extracted by the addition of hexane and partitioning. Residual water was removed from the organic phase with $MgSO_4$, and the reaction product dodecyldimethylsilylmethyl acetate was concentrated under vacuum.

Trans-esterification of Dodecyldimethylsilylmethyl acetate with Methanol. Dodecyldimethylsilylmethyl acetate was dissolved in methanol, freshly prepared NaOMe was added to adjust pH>10, and the reaction mixture heated to reflux. The reaction was allowed to proceed to completion, and then concentrated under vacuum. The reaction product was extracted by the addition of hexane and partitioning. Residual water was removed from the organic phase with $MgSO_4$, and the reaction product dodecyldimethylsilylmethyl alcohol was concentrated under vacuum.

Conversion of Dodecyldimethylsilylmethyl alcohol to the chloroformate. Triphosgene was dissolved with stirring in $CH_2Cl_2$ at 10° C. under $N_2$. Subsequently, $Na_2CO_3$ was added, followed by the addition of dodecyldimethylsilylmethyl alcohol (in $CH_2Cl_2$) such that the temperature was maintained below 10° C. The reaction was allowed to proceed to completion. The reaction product, a precipitate, was collected and washed with PhCH₃.

Conversion of Dodecyldimethylsilylmethyl chloroformate to the N-hydroxy-succinimidyl carbonate. Dodecyldimethylsilylmethyl chloroformate was dissolved in $CH_2Cl_2$ and cooled in an ice/acetone bath to ~10° C. N-hydroxy-succinimide was added in a bolus, with $Et_3N$ added dropwise to maintain the temperature below 20° C. An aliquot of saturated aqueous $NaHCO_3$ was added and the mixture allowed to partition. The organic phase contained the reaction product. Residual water was removed from the organic phase with $MgSO_4$, and the reaction product was concentrated under vacuum. Residual water was removed from the organic phase with $MgSO_4$, and the reaction product dodecyldimethylsilylmethyl N-succinimidyl carbonate was concentrated under vacuum.

Conjugation of Heparin to give dodecyldimethylsilylmethyl heparin carbonate. Sodium heparin was dissolved in water to give a 20% solution. Aliquots of DMF and dimethyl aminopipiridine added. Dodecyldimethylsilylmethyl N-succinimidyl carbonate dissolved in DMF was added dropwise over at least 2 hours. The crude product was triturated with and collected by filtration. Water was removed by evaporated in a vacuum desiccator. The ivory powder was purified by continuous extraction with acetone in a large soxhlet extractor for ~3 days.

Coating solution. The silyl-heparin complex was dissolved in water to a concentration of 1%. Isopropanol was added slowly with mixing such that the final concentration of isopropanol was 60% and the final concentration of silyl-heparin was 0.25%. For use in coating, devices were immersed for 30 minutes at 56° C., rinsed in water and air-dried at 56° C. for 1 hour.

EXAMPLE 2

Binding of Growth Factors to Adsorbed Silyl-Heparin

All silyl-heparin variants bound FGF-2, used as a model growth factor, when used as a coating as determined by immunoassay. The chromogenic signal generated in the assay of bonded FGF-2 (100 ng) was similar regardless of the silyl-heparin variant used, and the background with silyl-heparins with no FGF-2 was low.

Figure 2:
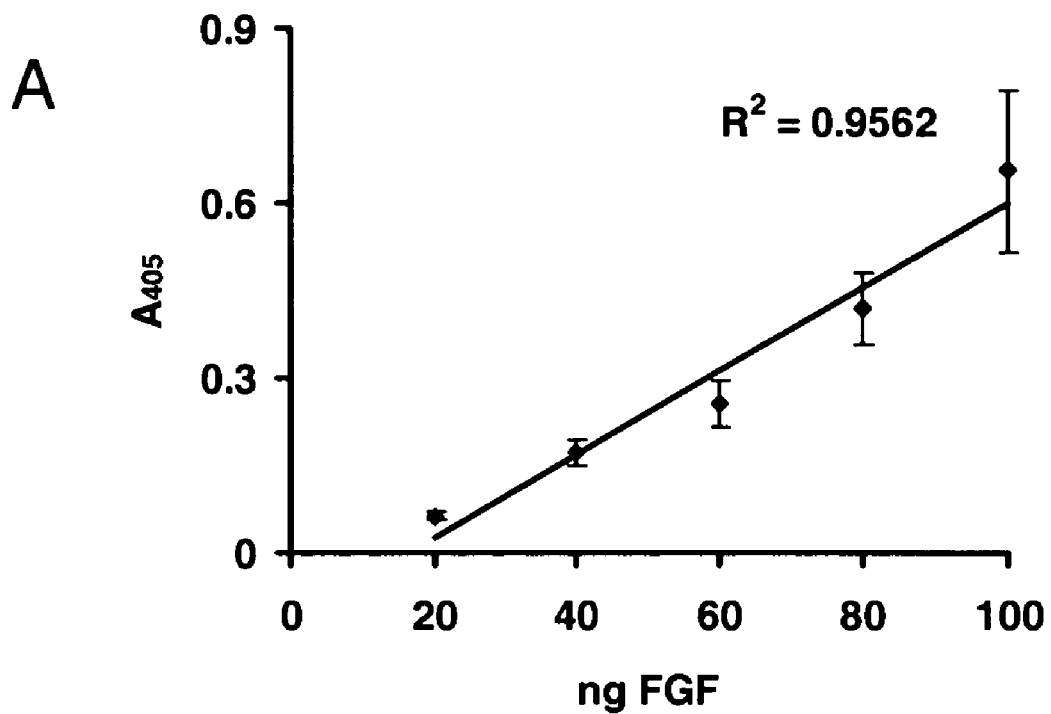
FIG. 2 illustrates that the amount of FGF-2 bonded to the silyl-variant of Formula I (n=3, x=6) was directly related to the amount offered for binding. FGF-2 was detected over a wide range of concentrations from at least 100 ng to 20 ng (A) and from at least 25 ng to as low as 5 ng (B).
Figure 2:
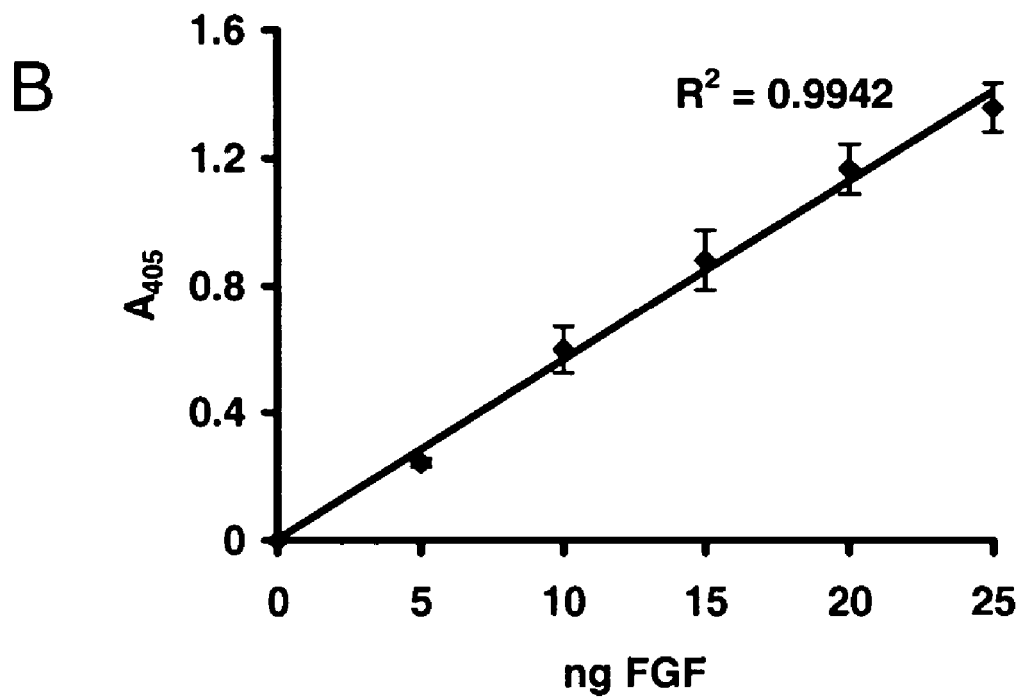

Additional studies were done on the silyl-variant of Formula I where n was 3 and x was 6. The amount of FGF-2 bonded to silyl-heparin was directly related to the amount offered for binding as illustrated in FIG. 2. FGF-2 was detected over a wide range of concentrations from at least 100 ng to as low as 5 ng. In control studies, when an irrelevant antibody (anti-TGF-betaRII) was used instead of anti-FGF-2, no signal was generated. The color development was linear at higher concentrations indicating that under the conditions of the assay the upper saturation limit of the silyl-heparin had not been reached. The surface area used for coating was estimated to be approximately 0.35 cm².

To establish if silyl-heparin could also bind other growth factors, VEGF and bone morphogenic protein-2 (BMP-2) were also used. VEGF was also detected over a range similar to that of FGF-2, and BMP-2 also complexed to silyl-heparin.

Figure 3:
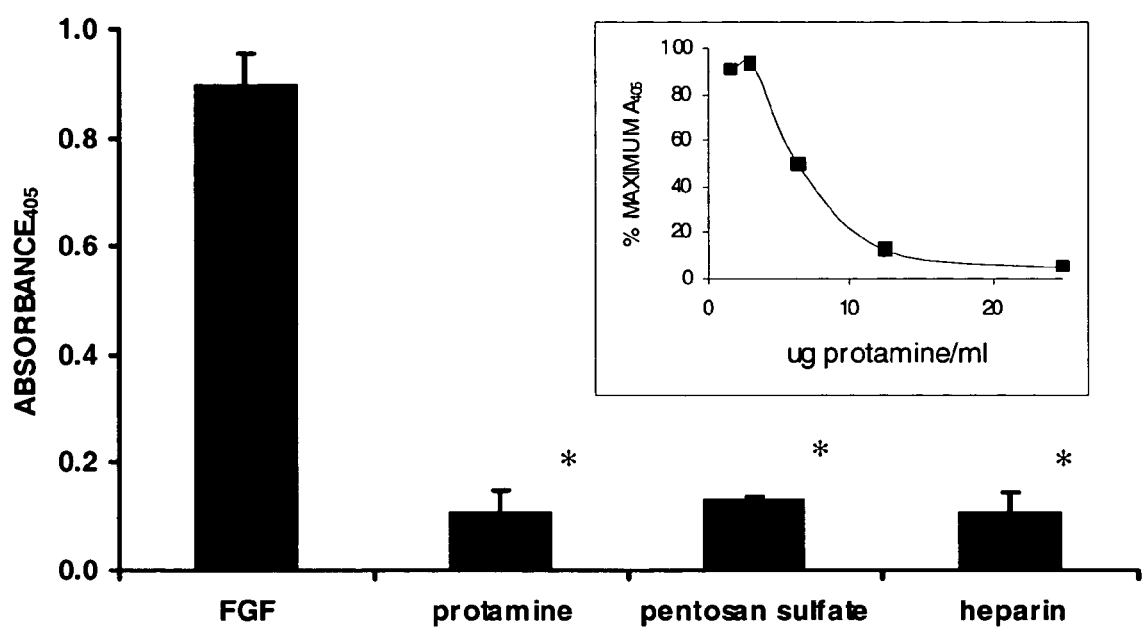
FIG. 3 illustrates silyl-heparin-FGF-2 binding inhibition by agents known to interfere with heparin-FGF-2 binding. Protamine sulfate, pentosan sulfate, and a large molar excess of heparin were added during the assay. All three agents blocked the binding of heparin to FGF-2. The inset shows that all three inhibitors exhibited concentration dependent effects.

To establish if binding of FGF-2 to silyl-heparin could be blocked by agents known to interfere with heparin-FGF-2 binding, protamine sulfate, pentosan sulfate, and a large molar excess of heparin were added during the assay. All of these agents inhibited the binding of FGF-2 to silyl-heparin (FIG. 3). All of the inhibitors demonstrated concentration dependant effects (FIG. 3, insert).

EXAMPLE 3

Binding of Silyl-Heparin-Growth Factors to Medical Films

A number of medical films were evaluated for their ability to support attachment of silyl-heparin, including films made of co-polyesters, polyurethanes, ethyl vinyl acetate, and polyether block amide. The binding of silyl-heparin to various types of medical films is shown in Table 1. Heparin was detected using a commercially available kit that measures the heparin-based inhibition of factor Xa. All of these films bound silyl-heparins. The most effective film was polyurethane followed by ethyl vinyl acetate, polyether block amides, and co-polyesters. The silyl-heparin coated films were stained with dimethyl methylene blue (DMMB) and examined visually. Polyurethane and ethyl vinyl acetate (EVA) films were stained uniformly. The co-polyesters and polyether block amide could not be detected by staining. Similar staining patterns were observed regardless of the variant of silyl-heparin used. Polyurethane films and EVA films coated with silyl-heparin of Formula I wherein the bioactive molecule was FGF-2 were subsequently used in immunoassays and FGF-2 was detected.

TABLE 1

| Film Type | mIU heparin/cm² |
| --- | --- |
| co-polyester 325 | 10 |
| co-polyester 330 | 9 |
| co-polyester 390 | 18 |
| polyurethane 437 | 83 |
| ethyl vinyl acetate 500 | 32 |
| ethyl vinyl acetate 501 | 17 |
| polyether block amide 820 | 11 |
| polyether block amide 840 | 13 |

Figure 4:
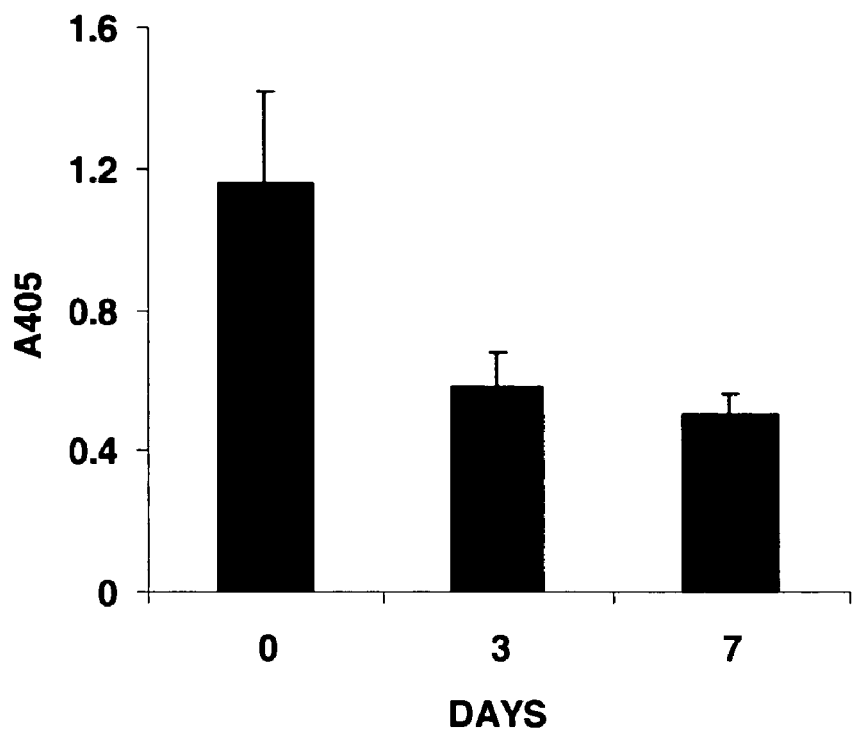
FIG. 4 illustrates the detection of FGF-2 on ethyl vinyl acetate (EVA) films pre-coated with FGF-2 and silyl-heparin and incubated in tissue culture medium for up to 7 days. The films were assayed for FGF-2 using immunological methods. The values represent the average of triplicate evaluations±S.D.

One of the underlying hypotheses supporting the use of silyl-heparins for binding growth factors is that the silyl-heparin-FGF can be slowly released from the films. This release could then affect cells in the local area. To establish that growth factors applied to the films would be released from the films, EVA films were coated with the silyl-heparin of Formula I, wherein the bioactive molecule was FGF-2, and incubated in medium for up to 7 days. The films were then assayed for the presence of FGF-2 on the film (FIG. 4). The amount of FGF-2 decreased over time, although by day 7 there was still detectable FGF-2 on the films.

EXAMPLE 4

Production of Bioactive Films Based on Polyethylene Vinyl Acetate and Coated with Growth Factor Plus Antibiotic Medical films composed of poly ethylene vinyl acetate (pEVA) were purchased commercially as 2 mil thick sheets. The films, with a paper protective backing, were cut into appropriately sized rectangles. The protective backing on the films was removed and the films rinsed in water. The films were immersed for 30 minutes in a solution of aqueous 60% isopropanol containing 0.25% of the silyl-variant of Formula II where n was 4 and x was 4. The films were rinsed in several changes of water and air-dried at 56° C. The films were then floated on a solution of phosphate buffered saline containing nanogram amounts of basic fibroblast growth factor (FGF-2) for 30 minutes. This incubation allowed the FGF-2 to complex to the film-bonded silyl-variant of Formula II, resulting in a complex of Formula I. The films were then rinsed by serial transfer to phosphate buffered saline containing 50 µg/mL of gentamicin sulfate. The rinse was intended to remove unbound complexes of Formula I, and to further complex gentamicin to the film.

The film was then placed over an adhesive bandage such that the film adhered to the bandage with the FGF-2 side facing the air.

EXAMPLE 5

Production of Bioactive Films Based on Polyurethane and Coated with Growth Factor Plus Antibiotic Medical films composed of polyurethane were purchased commercially as 1 mil thick sheets. The films, with a paper protective backing, were cut into appropriately sized rectangles. The protective backing on the films was removed and the films rinsed in water. The films were immersed for 30 minutes in a solution of aqueous 60% isopropanol containing 0.25% of the silyl-variant of Formula II where n was 4 and x was 4. The films were rinsed in several changes of water and air-dried at 56° C. The films were then floated on a solution of phosphate buffered saline containing nanogram amounts of basic fibroblast growth factor (FGF-2) for 30 minutes. This incubation allowed the FGF-2 to complex to the film-bonded silyl-variant of Formula II, resulting in a complex of Formula I. The films were then rinsed by serial transfer to phosphate buffered saline containing 50 µg/mL of gentamicin sulfate. The rinse was intended to remove unbound complexes of Formula I, and to further complex gentamicin to the film. In some cases the synthetic peptide F2A3 was used rather than FGF-2.

EXAMPLE 6

In vitro Stimulation of Cell Growth

The effect of the silyl-variant of Formula I on cell proliferation in vitro was evaluated by floating coated films on media overlying endothelial cells in culture. Aliquots of $10^4$ cells were seeded into individual wells of 24-well cluster plates and allowed 24 hours to attach to the substrate. The medium was changed to one containing 2% serum, and 1.1 cm diameter discs of ethyl vinyl acetate (EVA) were introduced into the culture. The discs floated over the cells at the air-water interface, with the growth factor coating facing the medium. The discs were previously treated such that they were sham coated with the silyl-variant of Formula II or the silyl-variant of Formula I where the bioactive molecule was FGF-2 (10 ng or 100 ng). Control groups were uncoated. The films persisted to float on top of the medium throughout the experiment.

Figure 5:
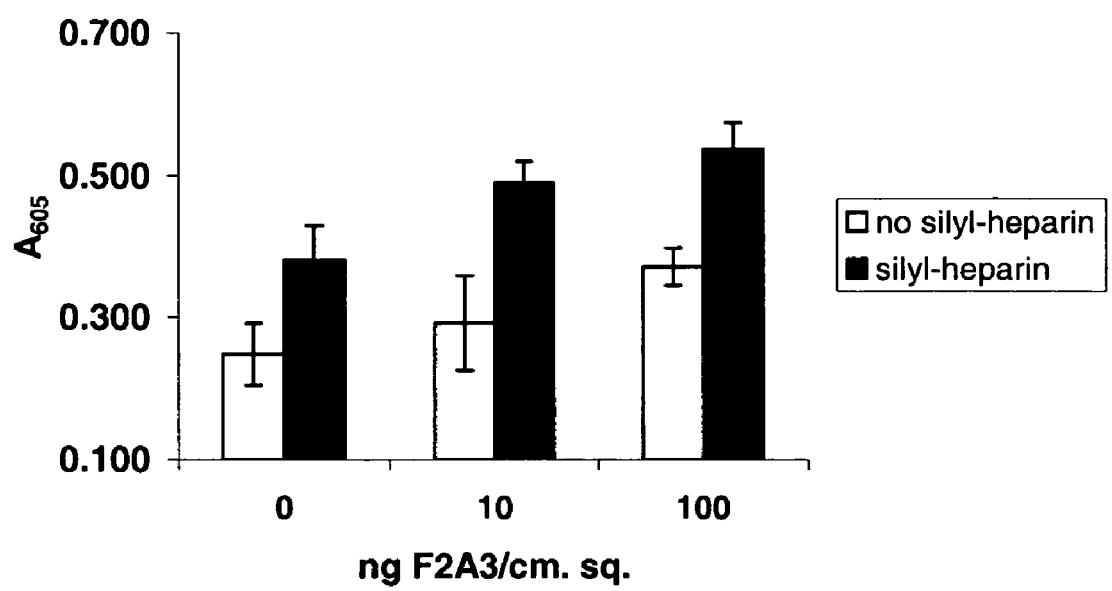
FIG. 5 illustrates the growth of rat microvascular endothelial cells cultured in the presence of "rafts" of coated films. Cells were cultured in a low-serum medium for 3 days after which the relative cell concentration was determined by staining fixed cells with crystal violet. The subsequently dissolved stain was detected at 605 nm. The data are presented as the mean±S.E.

Endothelial cells exposed to the films coated with the silyl-variant of Formula I where the bioactive molecule was FGF-2 underwent a dose-dependant increase in growth (FIG. 5). Films coated with only silyl-heparin of Formula II did not demonstrate a significant increase in growth.

To evaluate if the growth observed with film coated with the silyl-variant of Formula I where the bioactive molecule was FGF-2 could be obtained with other types of growth factors, films were coated directly with F2A3 or with silyl-heparin plus F2A3. The results indicated that silyl-heparin plus F2A3 was effective in simulating cell growth and was more effective than a coating of F2A3 alone. Similar results were obtained with FGF-2 and silyl-heparin plus FGF-2, demonstrating that the silyl-heparin played a key role.

EXAMPLE 7

Production of a Bandage Coated with the Silyl-Variant of Formula I (n=4, x=4) and Gentamicin Commercially available adhesive wound dressings (Coverlet®, Beiriersdorf-Jobst, Inc.) were peeled open to expose the dressing. The dressing is composed of a gauze pad with an attached polymeric film of polyurethane. The polyurethane film is intended to minimize adhesion of the bandage to the wound. The gauze pad, and attached polyurethane film, was immersed in a solution of aqueous 60% isopropanol containing 0.25% of the silyl-variant of Formula II where n was 4 and x was 4. That heparin was bonded to the films was verified by staining with the heparin specific dye dimethyl methylene blue. The films were then rinsed in several changes of water containing gentamicin (250 µg/mL) and air-dried at 56° C.

EXAMPLE 8

Use of Bioactive Films on Full Thickness Wounds

Polyurethane films were coated with growth factor plus antibiotic as in Example 5 above. The films were placed over a saline-moistened, non-bleeding full thickness wound in adult rats. The wound was made by cutting the skin down to the level of the fascia with surgical scissors to make a full thickness wound with dimensions of approximately 1 cm×1 cm. The bioactive film was covered with a bandage. The wound site was then covered with wound wrapping to minimize the ability of the animal to remove the dressing. The animals were allowed 10 days for healing.

The wound tissue was processed for histology by standard methods. Sections were cut and stained with either hematoxylin and eosin (H&E) or Masson's trichrome stain. The extent of dermis and organization were assessed by examination of slides stained with H&E. Collagen was assessed using Masson's trichrome stain. Keratin was assessed by examining specimens stained with H&E, and specimens stained separately with Masson's trichrome stain. Relative capillary density was determined with specimens stained with Masson's trichrome at a magnification of 400×, and determinations were made for each specimen in at least two different locations of the wound just below the wound edge (open label). Specimens were read as blind samples and scored with a ranking of 0-5 with 5 being similar to normal tissue.

The morphological scores from full thickness dermal wounds in normal rats after 10 days are shown in Table 2. Specimens were read as blind samples and scored with a ranking of 0-5 with 5 being similar to normal tissue. The data was expressed as the average from 9 specimens± standard error. The Mann-Whitney Rank Sum Test was used to assess statistical significance (P) for all comparisons except for capillary density where Student's t-test was used.

TABLE 2

|  | CONTROL | | SILYL-HEPARIN PLUS FGF-2 | | |
| --- | --- | --- | --- | --- | --- |
|  | AVERAGE | S.E. | AVERAGE | S.E. | P |
| Neo-epithelization | 1.2 | 0.3 | 2.3 | 0.9 | 0.03 |
| Organization of mesenchyme | 1.2 | 0.18 | 2.3 | 0.3 | 0.01 |
| Presence of keratin | 0.1 | 1.2 | 1.1 | 0.3 | 0.003 |
| Presence of collagen | 0.2 | 0.1 | 0.9 | 0.3 | 0.03 |
| Capillary density | 31.0 | 3.7 | 16.2 | 1.9 | 0.001 |

After 10 days the use of films coated with silyl-heparin plus FGF-2 resulted in increases in healing as measured by new epidermis, increased collagen and keratin, and organization of the mesenchyme. There was a decrease in capillary density. A similar morphological response was found in wounds covered with a film coated with the silyl-heparin plus the bioactive molecule F2A3.

Figure 6:
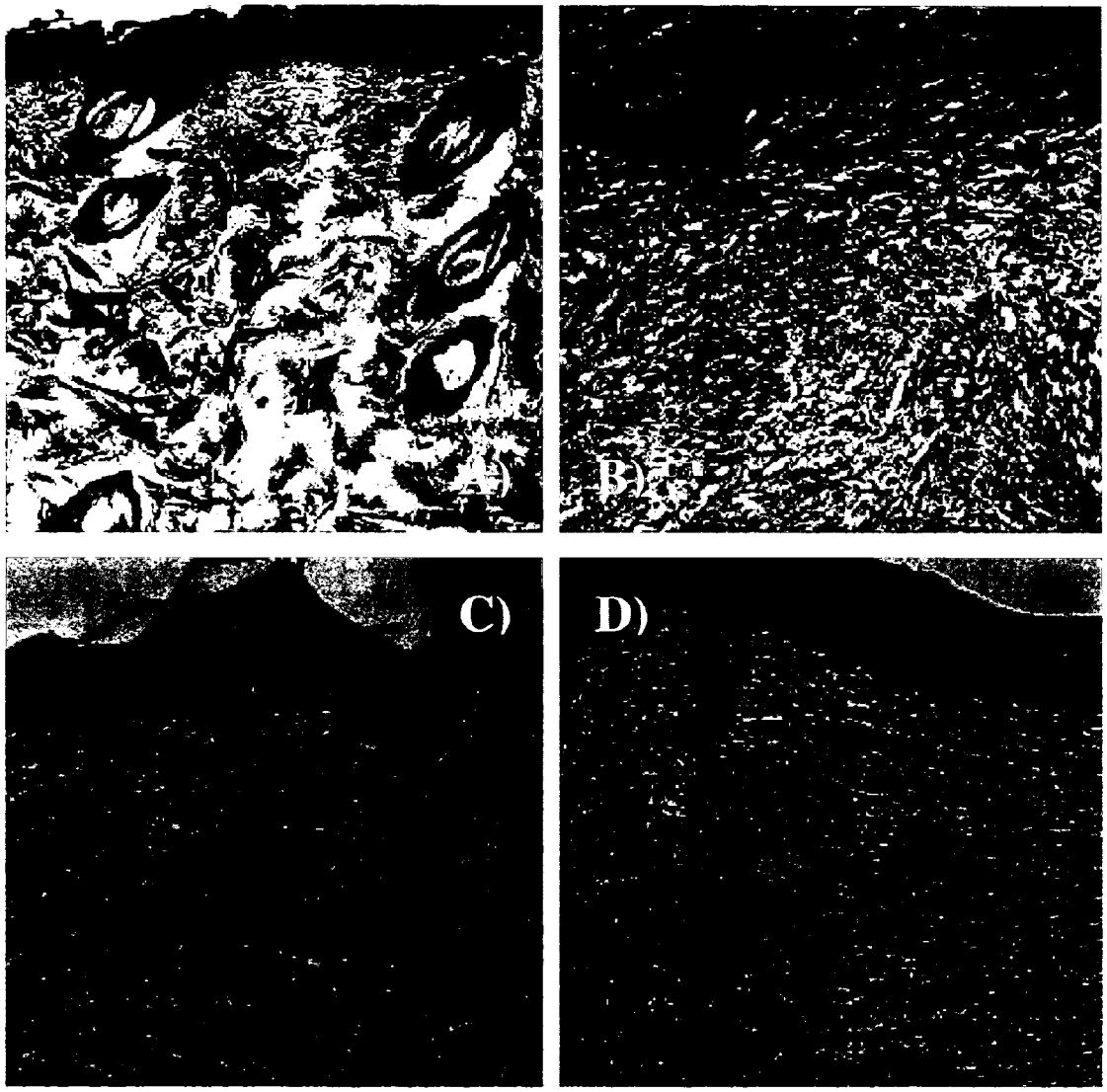
FIG. 6 shows full-thickness skin wounds in normal adult rats covered with a polyurethane film with and without a silyl-heparin-growth factor coating. In normal skin, collagen deposition can be seen in dermis as intensive blue stain (A). Wounds were covered with uncoated film (B), film coated with silyl-heparin-FGF-2 (C), or film coated with silyl-heparin-F2A3 (D). On day 10, wound areas were dissected; collagen is visualized by trichrome stain. The area of the wound presented is adjacent to the wound edge. Masson's trichrome stain was used; the original magnification was 100×.

The morphological appearance of wound margins is illustrated in FIG. 6 where an increase in collagen was found in wounds treated with silyl-heparin plus growth factor (FGF-2 or F2A3). Compared to control wounds the granulation tissue in wounds covered with a film coated with either silyl-heparin plus FGF or silyl-heparin plus F2A3 exhibited significantly more collagen deposition, lower vascularity, and lower cellularity. Furthermore the cells were oriented in a more orderly fashion and parallel to the dermis.

The lower level of vascularity is presumptively due to an acceleration of the normal healing process that involves an initial increase in vascularity in the first few days after wounding followed by a decrease in vascularity and cellularity. The orderly orientation of the mesenchymal layer is presumptively due to tissue tension and is indicative of an active contraction process. Collectively, these demonstrate that the wounds covered with a film coated with silyl-heparin plus a growth factor were in a more mature stage of wound healing than control wounds.

Figure 7:
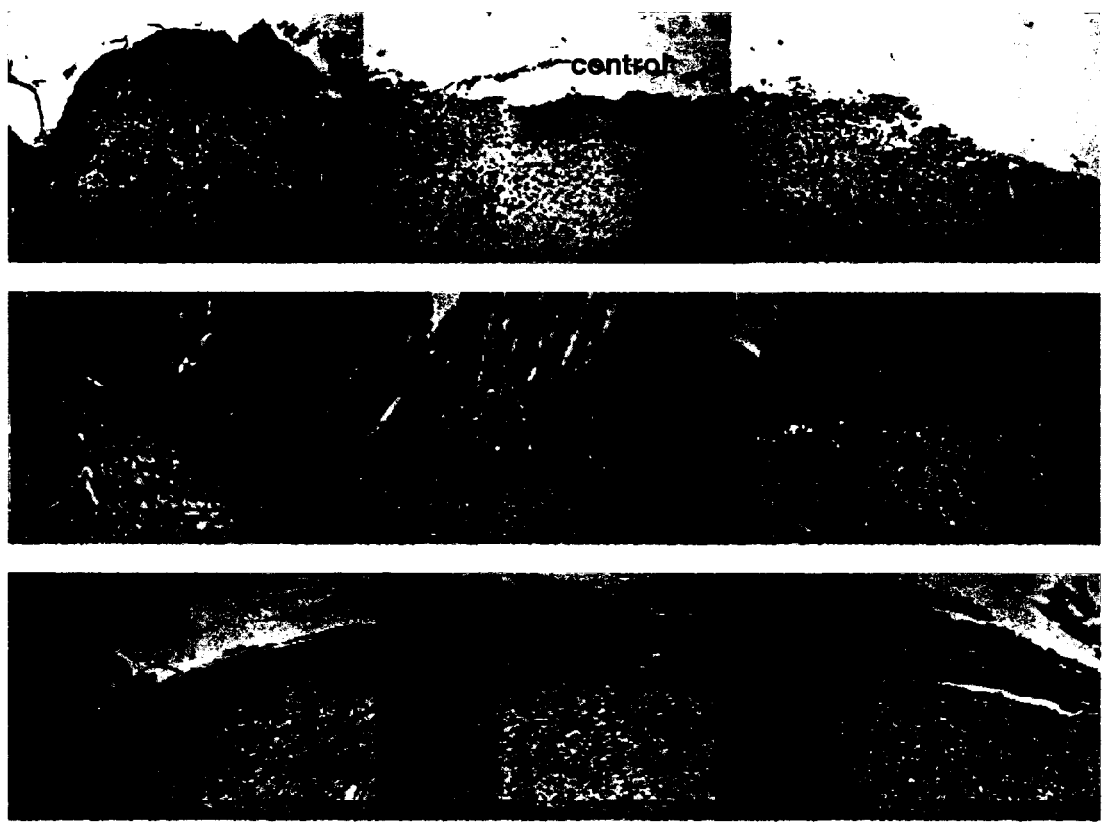
FIG. 7 illustrates the re-epithelialization of full-thickness dermal wounds in rats at 10 days after wounding and covering with polyethylene films (1 mil) with no coating (control), silyl-heparin-FGF-2, or silyl-heparin-F2A3. The silyl-heparin variant used was a molecule of Formula I (n=4, x=4). FGF-2 was used at a target dose of 50 ng/cm$^2$, and F2A3 at a target dose of 100 ng/cm$^2$. A hematoxylin and eosin (H&E) stain was used.
Figure 8:
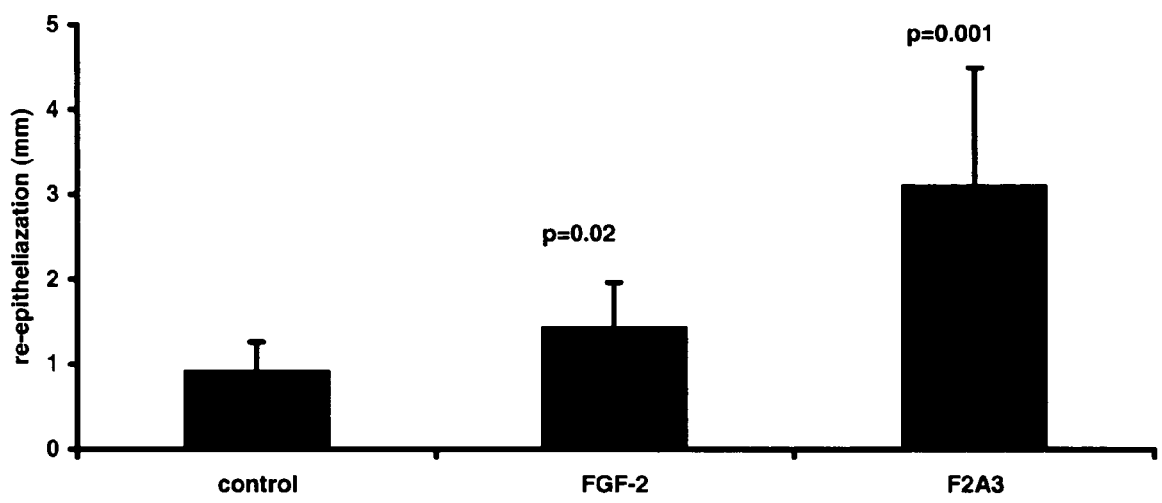
FIG. 8 illustrates the neo-epithelialization of full thickness wounds in rats after 10 days. Wound areas were covered with polyurethane films coated with or without silyl-heparin-FGF-2 or silyl-heparin-F2A3.

To more fully examine the re-epithelization of the wound area, the length of the keratinocyte layer was quantitated by measuring the length of the epithelial sheet from the leading edge to the wound margin from sections taken from the middle of the wound area. Wounds covered with coated films of either silyl-heparin-FGF-2 or silyl-heparin-F2A3 had significantly longer epithelial layers compare to films with no coating (FIGS. 7 and 8).

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A wound dressing comprising a polymeric film having complexed thereto by hydrophobic interaction a construct comprising a polyanion covalently bonded to a hydrophobic prosthetic moiety, with a first bioactive molecule directly complexed to the polyanion wherein the polyanion is a construct of Formula I:

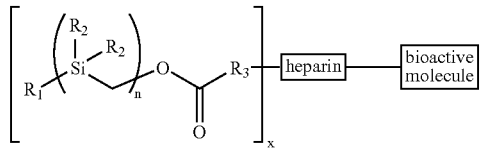

wherein
$R_1$ is an $C_{1-18}$ alkyl or $C_{6-32}$ aryl group,
each $R_2$ is independently selected from the group consisting of $C_{1-18}$ alkyl and $C_{6-32}$ aryl,
$R_3$ is N or O,
n is a number from 1 to 10,
x is a number from 1 to about 30, and
heparin is a heparin-activity molecule bonded to $R_3$ via a covalent bond, thereby forming a silyl-heparin covalent complex, with a first bioactive molecule directly complexed to the heparin-activity molecule.

2. The wound dressing of claim 1, wherein the silyl-heparin covalent complex has a dissociation rate from the polymeric film determined by the value of n and x.

3. The wound dressing of claim 1, wherein the silyl-heparin covalent complex comprises [benzyl-bis(dimethylsilylmethyl)]-(N-heparinyl)-carbamate or [benzyl-tris(dimethylsilylmethyl)]-(N-heparinyl)-carbamate.

4. The wound dressing of claim 1, wherein the heparin-activity molecule is heparin, heparan sulfate, hyaluronic acid, dextran, dextran sulfate, chondroitin sulfate, dermatan sulfate, a molecule including a mixture of variably sulfated polysaccharide chains composed of repeating units of D-glucosamine and either L-iduronic or D-glucuronic acids, salts of any of the foregoing, derivatives of any of the foregoing, or combinations of any of the foregoing.

5. The wound dressing of claim 1, wherein said first bioactive molecule is directly complexed to the heparin-activity molecule by affinity complexation.

6. The wound dressing of claim 1, wherein the molecule of Formula I comprises an n value equal to 4 and an x value equal to 4.

7. The wound dressing of claim 1, wherein the molecule of Formula I comprises an n value equal to 2 and an x value equal to 6.

8. A method for making a wound dressing, comprising:
providing a wound contacting polymeric film;
providing a molecule of Formula II:

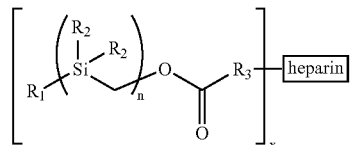

wherein
$R_1$ is an $C_{1-18}$ alkyl or $C_{6-32}$ aryl group,
each $R_2$ is independently selected from the group consisting of $C_{1-18}$ alkyl and $C_{6-32}$ aryl,
$R_3$ is N or O,
n is a number from 1 to 10, and
heparin is a heparin-activity molecule bound to the silyl moiety via covalent bonding, wherein x is from 1 to about 30 for each heparin-activity molecule, thereby forming a silyl-heparin complex;
attaching the sily-heparin complex of Formula II to the polymeric film by hydrophobic interaction; and
attaching a first bioactive molecule to the heparin-activity molecule.

9. The method of claim 8, wherein providing the molecule of Formula II further comprises selecting a dissociation rate of the molecule of Formula II from the polymeric film determined by the value of n and x.

10. The method of claim 8, further comprising attaching a second bioactive molecule to the heparin-activity molecule.

11. The method of claim 10, wherein the second bioactive molecule is an antibiotic.

12. A method for treating a wound, comprising:
providing a wound dressing of claim 1; and
contacting the wound dressing to the wound.

13. The method of claim 12, wherein the wound dressing comprises a silyl-heparin complex that has a dissociation rate from the contacting surface determined by the value of n and x.

14. The method of claim 12, wherein the wound dressing comprises a [benzyl-bis(dimethylsilylmethyl)]-(N-heparinyl)-carbamate or [benzyl-tris(dimethylsilylmethyl)]-(N-heparinyl)-carbamate silyl-heparin complex.

15. The method of claim 12, wherein the wound is a surface lesion.

16. The method of claim 12, wherein the wound is an internal wound.

17. The method of claim 16, wherein the wound dressing comprises a biodegradable polymeric film.

18. The method of claim 12, wherein the wound dressing comprises a first bioactive molecule that is an adhesive molecule, whereby the contacting surface is non-thrombogenic and promotes cellular adhesion.

19. The method of claim 12, wherein the wound dressing further comprises a second bioactive molecule.

20. The method of claim 19, wherein the second bioactive molecule is an antibiotic.

* * * * *